United States Patent [19]

Turner et al.

[11] Patent Number: 4,764,625

[45] Date of Patent: Aug. 16, 1988

[54] PROCESS FOR PREPARING ARYLAMINES

[75] Inventors: S. Richard Turner, Pittsford; John F. Yanus; Dale S. Renfer, both of Webster, all of N.Y.

[73] Assignee: Xerox Corporation, Stamford, Conn.

[21] Appl. No.: 639,032

[22] Filed: Aug. 9, 1984

Related U.S. Application Data

[63] Continuation-in-part of Ser. No. 215,610, Dec. 10, 1980, abandoned, which is a continuation-in-part of Ser. No. 118,147, Feb. 4, 1980, abandoned.

[51] Int. Cl.$^4$ .................. C07C 87/64; C07C 87/58; C07C 87/56; C07C 87/54
[52] U.S. Cl. .................. 548/442; 564/309; 564/405
[58] Field of Search ............. 564/405, 309; 548/442

[56] References Cited

U.S. PATENT DOCUMENTS

| | | | |
|---|---|---|---|
| 2,476,170 | 7/1949 | Widiger, Jr. | 260/576 |
| 2,924,620 | 2/1960 | Miller | 260/576 |
| 3,065,269 | 11/1962 | Dente | 260/576 |
| 3,251,881 | 5/1966 | Susi et al. | 260/576 |
| 3,313,854 | 4/1967 | Levy | 260/576 |
| 3,314,788 | 4/1967 | Mattor | 96/1.5 |

FOREIGN PATENT DOCUMENTS 507860 6/1939 United Kingdom .
1455207 11/1976 United Kingdom .

OTHER PUBLICATIONS

Creason et al, Jour. Org. Chem., vol. 37, No. 26, pp. 4440–4446, 1972.
F. Ullmann: Ueber eine neue Bildungsweise von Diphenylaminderivaten (Chem. Ber. 36, 2382, 1903).
Chemical Abstracts, vol. 70, No. 11, 1969, Columbus, OH, U.S.A., I. E. Moisak et al., "Tertiary Aromatic Amines," p. 289, Abstract 47064j, Izobiet., Prom. Obraztsy, Tovarnye Znaki, vol. 45, No. 29, 1968, p. 25, SU-A-226 629.

*Primary Examiner*—Floyd D. Higel
*Assistant Examiner*—Carolyn S. Greason
*Attorney, Agent, or Firm*—Peter H. Kondo

[57] ABSTRACT

The process of preparing a tertiary amine by the condensation of a mono- or di-tertiary amine and a mono- or di-iodoaryl compound. Conducting the condensation reaction in the presence of potassium hydroxide, and a copper catalyst, either in the absence of a solvent or with an inert saturated hydrocarbon solvent, in an inert atmosphere, at a temperature between from about 120° C. to about 190° C. for a period of time sufficient to at least substantially complete the reaction.

2 Claims, 3 Drawing Sheets

PROCESS FOR PREPARING ARYLAMINES

This is a continuation-in-part application based on Ser. No. 215,610, filed Dec. 12, 1980, which in turn is a continuation-in-part application based on Ser. No. 118,147, filed Feb. 4, 1980, the entire disclosures of both these applications being incorporated herein by reference and both abandoned.

This invention relates to an improved chemical process for the preparation of a class of tertiary amines. The reaction involved can be classified as a particular form of the Ullmann condensation reaction. More specifically, the reaction is limited to that between an aryliodide and an arylamine. In other words, the reaction involves the arylation of a secondary amine. The resulting product is a nonpolymeric compound or a polymeric compound depending upon the starting materials.

The chemical literature shows that the most useful synthesis of arylamines involves the coupling of a diarylamine and a haloaromatic compound, preferably an iodoaromatic compound, in the presence of a base and copper in a polar solvent. The reaction which led to this synthesis was discovered by F. Ullmann [Chem. Ber. 36, 2382 (1903)]. This reaction is difficult and possesses many undesirable features. Normally, a high temperature reaction, i.e. greater than 200° C., in a polar solvent with a copper catalyst and $K_2CO_3$ base is necessary to achieve arylation at a reasonable rate. In an analogous reaction, not within the scope of the present invention [S. C. Creason et al., J. Org. Chem., 37 4440 (1972)] a substituted aniline is reacted with iodobenzene at about 200° C. Potassium carbonate and copper are employed without a solvent. Ullmann reactions carried out in the manner described by Creason et al have not been found to be reproducible. These reactions require too high a temperature and are strongly dependent on the type and even the batch of copper catalyst used thereby introducing lack of control and lack of facileness. For example, 200° C. is approximately the minimum temperature that the process of Creason et al. reaction can be carried out with $K_2CO_3$. The intended products of these reactions are obtained in comparatively poor yields and usually require unreasonably long reaction times.

In U.S. Pat. No. 3,314,788, there is disclosed the reaction of a primary aryl diamine and an alkyl halide (see Col. 2, lines 39–47). This reaction is distinguished from the reaction product of a secondary diarylamine and an aryl halide. This latter reaction is said to be difficult and expensive and yields phenyl instead of benzyl derivatives. This reaction is included within the scope of the present invention and by the present process, it is no longer difficult and expensive.

It is an object of the present invention to present a process for the facile preparation of arylamines in comparatively high yields.

The foregoing object and others are accomplished in accordance with this invention by the process of preparing a tertiary amine by the condensation of a mono- or di-secondary amine and a mono- or di-iodoaryl compound.

The mono-secondary amine has the general formula $R_2R_3NH$ wherein $R_2$ and $R_3$ are the same or different members selected from the group consisting of alkyl, alkenyl, aryl, alkaryl and aralkyl. Examples of these amines are: 3-methyldiphenylamine, diphenylamine, diethylamine, etc.

The di-secondary amine has the general formula $R_4NH$—$R_1$—$NHR_4$ wherein $R_1$ is a divalent arylene or alkylidene group and $R_4$ is an aryl group. Examples of these amines are N,N'-diphenyl-[1,1'-biphenyl]-4,4'-diamine; N,-N'-diphenyl-[phenylene]-1,4-diamine; N,N'-diphenyl-[p,p''-terphenyl]-4,4''-di-amine; N,N'-diphenyl-[p,p'''-quatraphenyl]-4,4'''-diamine, 4,4'-isopropylidene bis(diphenylamine), etc.

Examples of mono and diiodoaryl compounds are: 4,4'-diiodobiphenyl; 1,-4-diiodobenzene; 4,4''-diiodoterphenyl; 1,6-diiodopyrene; 3,6-di-iodo-N-ethyl-carbazole; 4,4'''-diiodoquatraphenyl; 2,2-bis(4-iodophenyl)propane; iodobenzene; p-iodotoluene; etc.

It is obvious that when one of the reactants is monofunctional the resulting tertiary amine will be nonpolymeric. When the reactants are both difunctional a polymeric polytertiary amine will result.

The condensation reaction is conducted in the presence of potassium hydroxide and copper powder, either in the absence of a solvent or with an inert saturated hydrocarbon solvent, in an inert atmosphere at a temperature between about 120° C. and 190° C. for a period of time sufficient to substantially complete the reaction.

In prior art reactions leading to compositions formed by the present invention, significant variations in catalytic effect were observed when different copper catalysts were employed with potassium carbonate as the base. The use of KOH as the base significantly mitigated these variations. The mitigation was so great that it has been found that any finely divided copper catalyst can be employed so long as potassium hydroxide is employed as the base. Examples of copper catalysts are: copper powder, cupric oxide, cuprous oxide, cuprous sulfate, cuprous sulfide, etc. In fact, any copper catalyst heretofore commonly used in the Ullmann condensation reaction can be employed. In addition, the use of KOH allows shorter reaction times and lower reaction temperatures.

It has been found that a very efficient inert atmosphere is necessary for obtaining the intended product of the instant process. Inert atmospheres such as argon, nitrogen, or methane should be employed at the beginning of the reaction and, in particular, by the time the amine component is introduced into the reaction system.

In this reaction the ratio of base of amine should be such that the base is present as an excess in relation to the amine. This excess can range from about 1.5 to 1 up to 6 to 1 moles.

As indicated above, the use of KOH allows significant reduction in the reaction temperature as compared to prior art reactions employing $K_2CO_3$ as the base. The reaction range can be from 120° C. to 190° C. with the preferred reaction temperature being from 135° C. to about 165° C. At temperatures lower than about 125° C., the reaction does not proceed at a practical rate because the KOH/Cu does not form a melt until this temperature. 190° C. is the maximum temperature that is desirable using KOH due to very fast reactions, i.e. very short reaction times. With KOH, all batches of copper perform equally well. A sluggish copper catalyst in Creason et al [J. Org. Chem., 37 4440 (1972), described above] requiring a reaction time of greater than 3 days at 200° C. was found to give reaction time of 3–4 hours at 160° C. using KOH. A base is not present in the reaction to neutralize the liberated HI. The role of the base is to participate in the formation of a copper/amine complex which reacts with the iodo compound to form triarylamine. Although NaOH is a stronger base than K₂CO₃, reactions with NaOH are actually slower than with K₂CO₃. It is, therefore, clearly apparent that a base is not solely necessary for neutralization. All other bases are solids at reaction temperatures. Since KOH is a melt at 125° C. it mixes intimately with copper as well as the other reactants. Any commercially available KOH in flake or pellet form with a low water content can be employed. The flake form is preferred.

The process of the present invention can be carried out in the absence of a solvent when the intended product is very soluble at ambient temperature in the inert hydrocarbon solvent. When the intended product is at least relatively insoluble at ambient temperature in an inert hydrocarbon solvent, the use of KOH yields a relatively pure product which can be further highly purified by recrystallization from the same solvent.

An advantage of the instant process is the fact that relatively pure product can be obtained via the present process when KOH and an inert hydrocarbon solvent system is employed. This is distinguished from employing an aprotic or polar solvent. A further advantage gained from the use of an inert high boiling hydrocarbon solvent lies in the fact that the intended reaction product can be purified from the same solvent. This eliminates difficult handling conditions when a different solvent or purification means is employed. The inert aliphatic hydrocarbon can be dodecane, tetradecane or any other hydrocarbon having an initial boiling point about above 170° C. A particularly preferred material is Soltrol ® 170 initial b.p. 218° C. which is a mixture of $C_{13}$–$C_{15}$ aliphatic hydrocarbons and Soltrol ® 130 initial b.p. 176° C. available from Phillips Chemical Company. The Soltrol ® hydrocarbons dramatically reduced work-up times, yielded a much purer product and are less expensive solvents. Aprotic or polar solvents cannot be employed without formation of interfering and yield-reducing by-products.

BRIEF DESCRIPTION OF THE DRAWINGS

A more complete understanding of the process and device of the present invention can be obtained by reference to the accompanying drawings wherein.

Figure 1:
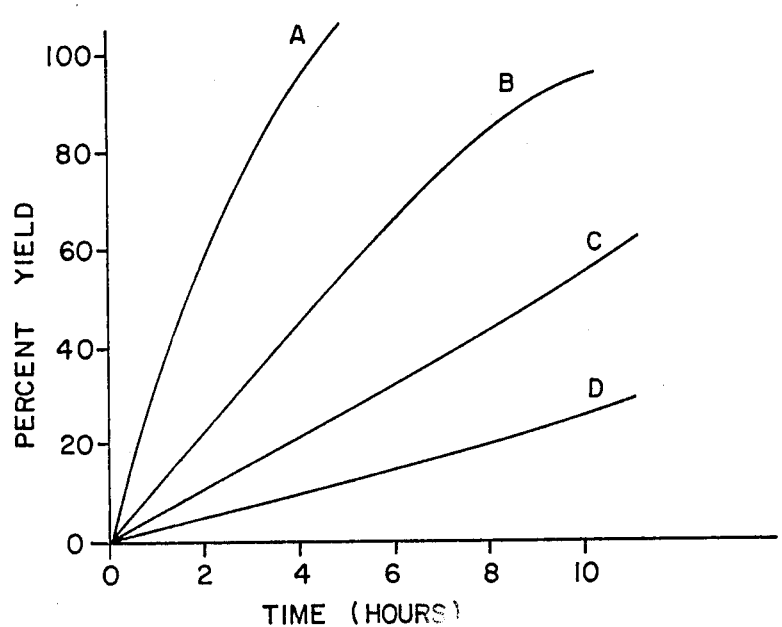
FIG. 1 graphically illustrates how different copper catalysts affect product yields for reactions employing with K₂CO₃.

The following examples are nonlimiting illustrations of the instant process.

EXAMPLE I

Preparation of N,N'-diphenyl-N,N'-bis(3-methylphenyl)-[1,1'-biphenyl]-4,4'-diamine having the following structural formula:

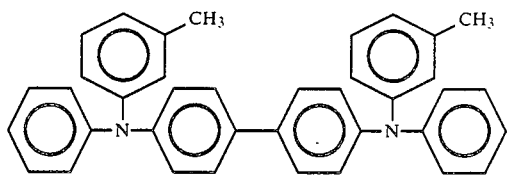

Into a 250 ml, three necked round bottom flask equipped with a mechanical stirrer, thermometer with temperature controller and purged with argon was placed 8.1 grams of diiodobiphenyl (0.02 mole), 14.6 grams 3-methyldiphenylamine (0.08 mole), 9 grams potassium hydroxide flake (0.16 mole), 6 grams of copper powder and 12 milliliters of Soltrol ® 170 (a mixture of $C_{13}$–$C_{15}$ aliphatic hydrocarbons from Phillips Chemical Company). The system was maintained under this inert atmosphere throughout the reaction. The contents were heated to 160° C. for about 5 hours with moderate stirring. The product was isolated by the addition of 150 mls. of Soltrol ® 170 and hot filtered (about 140° C.) to remove inorganic solids. The yellow filtrate was cooled with stirring yielding a yellow solid. The yellow solid was dissolved in toluene and column chromatographed using Woelm neutral alumina with toluene as eluent. A colorless solid was recovered from the mother liquors and recrystallized from n-octane to yield colorless crystals of the intended product, melting point 167°–168° C. with a yield of 85%.

EXAMPLE II

Preparation of N,N'-diphenyl-N,N'-bis(3-methylphenyl)-(p-terphenyl)-4,4''-diamine having the following structural formula:

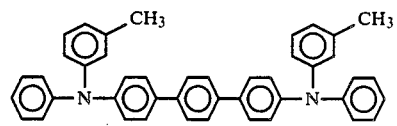

The same equipment and conditions as in example I were employed with the following charge: 9.6 grams (0.02 mole) of diiodoterphenyl, 14.6 grams (0.08 mole) of 3-methyldiphenylamine; 9.0 grams (0.16 mole) of potassium hydroxide flake, 6.0 grams of copper powder, and 12.0 milliliters of Soltrol ® 170. The above identified intended product was obtained as colorless crystals having a melting point of 188°–190° C. The yield was 75%.

EXAMPLE III

Preparation of N,N'-diphenyl-N,N'-bis[3-methylphenyl]-pyrenyl-1,6-diamine having the following structural formula:

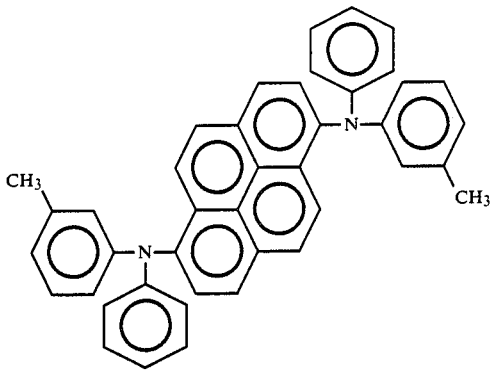

The same equipment and conditions as in Example I were employed with the following charge: 9.1 grams (0.02 mole) of 1,6-diiodopyrene, 14.6 grams (0.08 mole) of 3-methyldiphenylamine, 9.0 grams (0.16 mole) of potassium hydroxide flake, 6.0 grams of copper powder and 12.0 mls. of Soltrol ® 170. After column chromatographing the green filtrate using toluene as the eluent, the resulting deep yellow solid was extracted with acetone to yield yellow Crystals of the intended compound having a melting point of 236°–238° C. Yield 75%.

EXAMPLE IV

Preparation of N-ethyl-2,7-bis[N'-phenyl-N'-(3-methylphenyl)-amino]carbazole having the following structural formula:

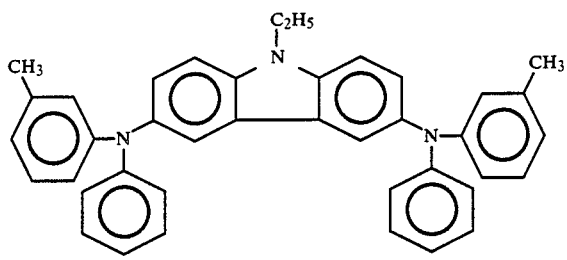

The same equipment and conditions as in Example I were employed with the following charge: 8.4 grams (0.02 moles) of 3,6-diiodo-N-ethylcarbazole, 14.0 grams (0.08 moles) 3-methyldiphenylamine, 9.0 grams (0.16 moles) of potassium hydroxide flake, 6.0 grams of copper powder and 12.0 milliliters of Soltrol ® 170. The above-identified product was obtained as a colorless solid having a melting point of 195°–197° C. Yield 72%.

EXAMPLE V

Preparation of N,N'-diphenyl-N,N'-bis-(3-methylphenyl)-[1,1'-biphenyl]-4,4'-diamine in the absence of the aliphatic hydrocarbon solvent.

A 500 milliliter 3 necked round bottom flask equipped with an argon purge, a condenser and an overhead mechanical stirrer was charged with 81.2 grams (0.2 mole) of 4,4'-diiodobiphenyl, 146.4 grams (0.8 mole) of 3-methyl-diphenylamine, 89.6 grams (1.6 moles) of KOH flake and 80 grams (1.0 mole) of copper powder. The flask was immersed in a 165° C. oil bath and the two-phase melt was stirred for 3 hours. Hot (140° C.) Soltrol ® 170 was added and the inorganic solid separated by vacuum filtration. On cooling, the product crystallized from the filtrate and was isolated in 89% yield by filtration. Purification was accomplished by slurrying the product with neutral alumina (10 grams) in 1 liter of Soltrol ® 170 at 150° C. for six hours, the alumina was removed by filtration and the purified product crystallized from the filtration on cooling. Isolation by filtration was accomplished with a 95% recovery of the product.

EXAMPLE VI

Preparation of N,N'-diphenyl-N,N'-bis(3-methylphenyl)-1,4-phenylenediamine having the following structural formula:

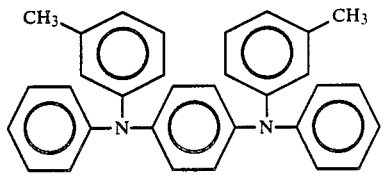

The same equipment and conditions as in Example I were employed with the following charge: 6.6 grams (0.02 mole) of 1,4-diiodobenzene, 14.6 grams (0.08 mole) of 3-methyldiphenylamine, 9.0 grams (0.16 mole) of potassium hydroxide, 6.0 grams of copper powder and 12.0 milliters of Soltrol ® 170. The above-identified intended product was obtained as a colorless product having a melting point 195°–197° C. Yield 81%.

EXAMPLE VII

Preparation of triphenylamine

The same equipment and conditions as in example I were employed with the following charge: 20.4 grams (0.1 mole) iodobenzene, 27.4 grams (0.15 mole) diphenylamine, 16.8 grams (0.3 mole) potassium hydroxide flakes, 15.0 grams of copper powder and 30.0 milliliters of Soltrol ® 170. The above-identified product was obtained as colorless crystals having a melting point of 125°–126° C. Yield 82%.

EXAMPLE VIII

Preparation of 3-methylphenyldiphenylamine

The same equipment and conditions as in example I were employed with the following charge: 20.4 grams (0.1 mole) iodobenzene, 27.5 grams (0.15 mole) 3-methyldiphenylamine, 15.0 grams copper powder and 30.0 milliliters of Soltrol ® 170. The above-identified intended product was obtained as colorless crystals having a melting point of 69°–70° C. Yield 75%.

EXAMPLE IX

This example details the preparation of a the polymer resulting from the condensation of 4,4'-isopropylidene bis(diphenylamine) and 4,4'-diiodobiphenyl.

In a 100 ml, three-necked round bottom flask equipped with a mechanical stirrer and purged with argon were placed 9.3 grams (0.025 mole) of 4,4'-isopropylidene bis(diphenylamine), 16.9 grams (0.3 mole) of potassium hydroxide flakes, 7.5 grams of copper powder and 25 milliliters of tetrahydronaphthalene. With the aid of an oil bath, the mixture was heated to 170° C. with stirring for one hour. The 4,4'-diiodobiphenyl, in the amount of 10.3 grams (0.025 mole), was added and the heterogeneous mixture allowed to stir for 18 hours. The reaction was cooled and 25 milliliters of tetrahydrofuran was added and brought to reflux. The liquid portion was decanted and the tetrahydrofuran reflux wash was repeated three times. The resulting solution was filtered and a fine yellow precipitate was formed upon addition to one liter of ethanol. The precipitate was dissolved in toluene and precipitated into acetone. This toluene-acetone sequence was repeated. The product was again dissolved in toluene and column chromatographed on Florisil, i.e. a magnesium silicate. The colorless eluent was precipitated into ethanol and dried to yield (65%) of a colorless powder. The polymer had an Mn of 10,000 and an Mw of greater than 20,000 as determined from a gel permeation chromatography analysis and vapor phase osmometry.

EXAMPLE X

Preparation of a polymer resulting from the condensation of N,N'-diphenyl[1,1'-biphenyl]-4,4'-diamine and 1,4-diiodobenzene In a 100 ml, three-necked round bottom flask equipped with a mechanical stirrer and purged with argon is placed 3.36 grams (0.01 mole) of N,N'-diphenyl-[1,1'-biphenyl]-4,4'-diamine, 4.5 grams of potassium hydroxide flakes, 3.0 grams of copper powder, 30 milliliters of tetrahydronaphthalene. With the aid of an oil bath, the mixture is heated to 150° C. for one hour. The 1,4-diiodobenzene, in the amount of 3.29 grams (0.01 mole), is added and the heterogeneous mixture is stirred at 150° C. for 3-4 hours. The mixture is filtered while hot. 25 milliliters of tetrahydrofuran is added and brought to reflux. The tetrahydrofuran reflux wash is repeated three times. The resulting solution is filtered and a precipitate formed by the addition of a liter of methanol. The precipitate is isolated and purified to a yield of 4.0 grams of the polymer.

EXAMPLE XI

Preparation of N,N'-diphenyl-N,N'-bis-(3-methylphenyl)-[1,1'-biphenyl]-4,4'-diamine in the absence of the aliphatic hydrocarbon solvent and in the presence of $K_2CO_3$ and different copper catalysts Numerous solventless reactions employing $K_2CO_3$ were carried out to attempt to use the process described by Creason et al [*J. Org. Chem.* 37 4440 (1972)] to prepare N,N'-diphenyl-N,N'-bis-(3-methylphenyl)-[1,1'-biphenyl]-4,4'-diamine (DBBD) by using a 250 ml three-necked round bottom flask equipped with a stirring shaft, stirrer bearing, a combination gas inlet and thermometer well and condenser. The flask was charged by adding 10.3 grams diiodobiphenyl (0.025 mole purified by methanol wash mp 203°-205° C.), 18.3 grams 3-methyl diphenylamine (0.1 mole distilled in vacuo giving an orange oil bp 140° C. @ 1 mm), 20.7 grams potassium carbonate (0.15 mole, J. T. Baker Chemical Co.) and 7.5 grams copper catalyst. The flask was immersed in the heating bath at about 200° C. and stirring was initiated (timing was begun at this point). Temperature control was achieved by immersing the flasks in a silicone oil both heated with immersion heaters controlled by $I^2R^R$ temperature controllers (Model L7-800). The temperature of the reaction mixture was monitored with a thermometer. Temperature was maintained within ±1° C. A pot temperature of 190° C. was achieved after about 5 minutes. The reaction was conducted for 4 hours. The initial light heterogeneous yellow color progressively darkened to a reddish copper color. Samples taken at various times were generally pale yellow in color. The results of these reactions are set forth in the table below. It should be noted that numerous experiments were required to discover that a copper bronze catalyst from Fison provided dramatically superior results over any other copper catalyst used.

| Catalyst (source) | Copper Conc'n (g/mol) | Temp. (pot °C.) | DBBD conversion (%) |
| --- | --- | --- | --- |
| None | — | 190 | <2% |
| Cu/Bronze (Fisons) | 100 | 190 | 85.7 |
| Cu (J. T. Baker Chem. Co.) | 300 | 190 | 9 |
| Cu (Matheson, Coleman & Bell) | 300 | 190 | 23 |
| Cu (Matheson, Coleman & Bell, 2nd batch) | 300 | 190 | 44 |
| Cu (1 micrometer) (Alfa) | 300 | 190 | 100* |
| Cu (10 micrometers) (Alfa) | 300 | 190 | 2.5 |
| Cu (freshly prepared) | 300 | 190 | 2.5 |
| Cu (Glidden-Durkee) | 300 | 190 | <2% |
| Cu (American Metal Climax, Inc.) | 300 | 190 | 10% |
| Copper resin (synthesized) | ~12 | 190 | 30 |
| Copper Zeolite (unknown) | — | 190 | 15 |

*large amount of side product

The results set forth in the table above clearly demonstrate that, except for the apparently unique copper bronze catalyst from Fison, poor yields are achieved with the materials and conditions described by Creason et al.

EXAMPLE XII

Preparation of N,N'-diphenyl-N,N'-bis-(3-methylphenyl)-[1,1'-biphenyl]-4,4'-diamine in the absence of the aliphatic hydrocarbon solvent and in the presence of $K_2CO_3$ and different copper catalysts Numerous additional solventless reactions employing $K_2CO_3$ were carried out to attempt to use the process described by Creason et al [*J. Org. Chem.*, 37 4440 (1972)] to prepare N,N'-diphenyl-N,N'-bis-(3-methylphenyl)-[1,1'-biphenyl]-4,4'-diamine (DBBD) by using a 250 ml three-necked round bottom flask equipped with a stirring shaft, stirrer bearing, a combination gas inlet and thermometer well and condenser. The flask was charged by adding 10.3 grams diiodobiphenyl (0.025 mole purified by methanol wash mp 203°-205° C.), 18.3 grams 3-methyl diphenylamine (0.1 mole distilled in vacuo giving an orange oil bp 140° C. @ 1 mm), 20.7 grams potassium carbonate (0.15 mole, J. T. Baker Chemical Co.) and 7.5 grams copper catalyst. The flask was immersed in the heating bath at about 200° C. and stirring was initiated (timing was begun at this point). Temperature control was achieved by immersing the flasks in a silicon oil bath heated with immersion heaters controlled by $I^2R^R$ temperature controllers (Model L7-800). The temperature of the reaction mixture was monitored with a thermometer. Temperature was maintained within ±1° C. A pot temperature of 190° C. was achieved after about 5 minutes. The reaction was conducted for 4 hours. The initial light heterogeneous yellow color progressively darkened to a reddish copper color. Samples taken at various times were generally pale yellow in color. The results of these reactions are set forth in the table below below. All of the following were carried out with copper bronze catalysts. The source of the catalyst is listed in the first column. It should again be noted that numerous experiments were required to discover that a copper bronze catalyst from Fison provided dramatically superior results over any other copper catalyst used.

| Catalyst (source) | Copper Conc'n (g/mol) | Temp. (pot °C.) | DBBD Conversion (%) |
| --- | --- | --- | --- |
| Cu/Bronze (Original batch, Fisons) | 300 | 190 | 92 |
| Cu/Bronze (Fisons 08, Fisons) | 300 | 190 | 100 |
| Cu/Bronze (Fisons 25, Fisons) | 300 | 190 | 52 |
| Cu/Bronze (BDH 6294850, British Drug House) | 300 | 190 | 45 |
| Cu/Bronze (British Drug House) | 300 | 190 | 68 |
| Cu/Bronze (BDH 2317880 Iron Cont., British Drug House) | 300 | 190 | 28 |
| Cu/Bronze (BDH 2317880, British Drug House) | 300 | 190 | 32 |
| Cu/Bronze (Natur Kupfer C, Venus) | 300 | 190 | 72 |
| Cu (J. T. Baker Chem. Co.) | 300 | 190 | 9 |
| Cu (1st Batch) (Matheson, Coleman & Bell) | 300 | 190 | 23 |
| Cu (2nd Batch) (Matheson, Coleman & Bell) | 300 | 190 | 44 |

The results set forth in the table above clearly demonstrate that, except for the apparently unique copper bronze catalyst from Fison, poor yields are achieved with the materials and conditions described by Creason et al.

EXAMPLE XIII

Preparation of N,N'-diphenyl-N,N'-bis-(3-methylphenyl)-[1,1'-biphenyl]-4,4'-diamine in the absence of the aliphatic hydrocarbon solvent and in the presence of $K_2CO_3$ and different copper catalysts Numerous solventless reactions employing $K_2CO_3$ were carried out to attempt to use the process described by Creason et al [J. Org. Chem., 37 4440 (1972)] to prepare N,N'-diphenyl-N,N'-bis-(3-methylphenyl)-[1,1'-biphenyl]-4,4'-diamine (DBBD) by using a 250 ml three-necked round bottom flask equipped with a stirring shaft, stirrer bearing, a combination gas inlet and thermometer well and condenser. The flask was charged by adding 10.3 grams diiodobiphenyl (0.025 mole purified by methanol wash mp 203°–205° C.), 18.3 grams 3-methyl diphenylamine (0.1 mole distilled in vacuo giving an orange oil bp 140° C. @ 1 mm), 20.7 grams potassium carbonate (0.15 mole, J. T. Baker Chemical Co.) and 7.5 grams copper catalyst. The flask was immersed in the heating bath at about 200° C. and stirring was initiated (timing was begun at this point). Temperature control was achieved by immersing the flasks in a silicone oil bath heated with immersion heaters controlled by $I^2R^R$ temperature controllers (Model L7-800). The temperature of the reaction mixture was monitored with a thermometer. Temperature was maintained within ±1° C. A pot temperature of 190° C. was achieved after about 5 minutes. The reaction was conducted for 4 hours. The initial light heterogeneous yellow color progressively darkened to a reddish copper color. Samples taken at various times were generally pale yellow in color. The percent yield in these reactions with copper bronze catalyst Batch #08 from Fison, copper bronze catalyst Batch #25 from Fison, copper (Matheson, Coleman & Bell) and copper (J. T. Baker Chem. Co.) are plotted against time and are shown as lines A, B, C, and D, respectively, in the graph illustrated in FIG. 1. It should be noted that numerous experiments were required to discover that only certain batches of copper bronze catalyst from Fison provided dramatically superior results over any other copper catalyst used. All other copper catalysts tested provided poor yields even under extended reaction times.

EXAMPLE XIV

Figure 2:
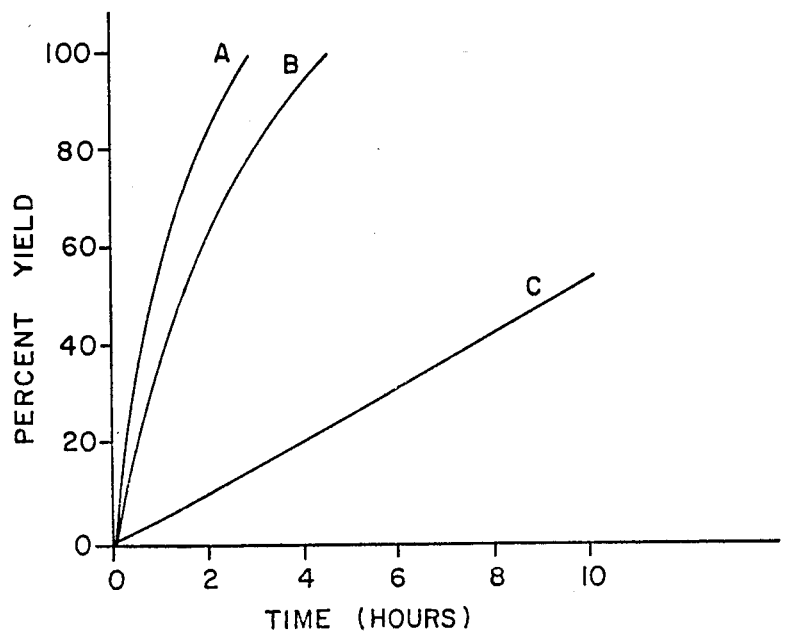
FIG. 2 graphically illustrates the effect of temperature on product yields.

Preparation of N,N'-diphenyl-N,N'-bis-(3-methylhenyl)-[1,1'-biphenyl]-4,4'-diamine at different temperatures in the absence of the aliphatic hydrocarbon solvent and in the presence of $K_2CO_3$ The procedures described in Example XIII were repeated with the same materials except that the only catalyst employed was Batch #08 from Fison and the reactions were conducted at temperatures of 220° C., 190° C., and 180° C. The percent yield in these reactions at temperatures of 220° C., 190° C., and 180° C. are plotted as lines A, B, and C, respectively, against time in the graph illustrated in FIG. 2. It should again be noted that numerous experiments were required to discover that a copper bronze catalyst from Fison provided dramatically superior results over any other copper catalyst used and that the reactions of this Example were conducted with the best catalyst known for the Creason et al process. The curves A, B, and C clearly demonstrate the adverse effect of lower reaction temperatures on the Creason et al process.

EXAMPLE XV

Figure 3:
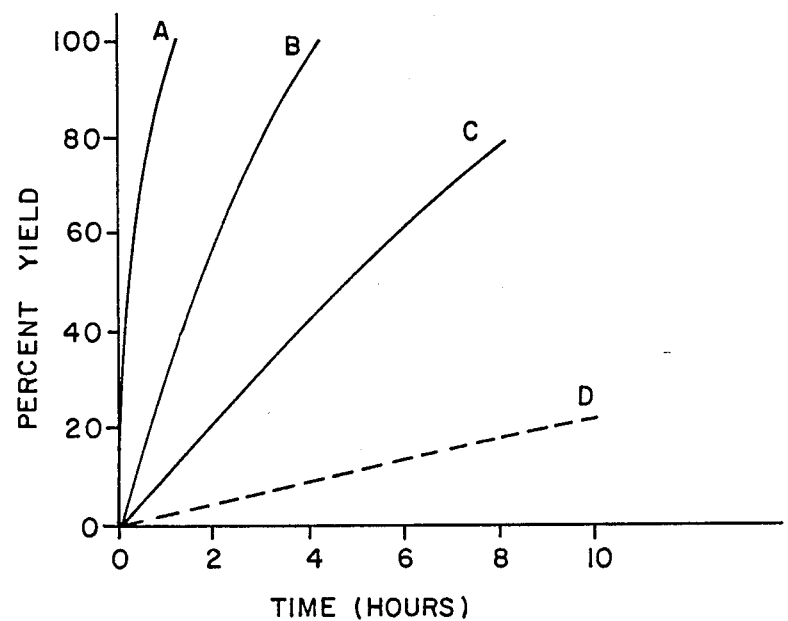
FIG. 3 graphically illustrates the effect of temperature on product yields and compares reactions employing KOH and K₂CO₃.

Preparation of N,N'-diphenyl-N,N'-bis-(3-methylphenyl)-[1,1'-biphenyl]-4,4'-diamine in the presence of KOH or $K_2CO_3$ Into a 250 milliliter, three-necked round bottom flask equipped with a mechanical stirrer, thermometer with a temperature controller and purged with argon was placed 10.3 grams of diiodobiphenyl (0.025 mole), 11.2 grams of potassium hydroxide flake (0.2 mole), 16.7 grams 3-methyldiphenylamine (0.1 mole), 7.5 grams copper (available from J. T. Baker Chemical Co.) and 15 milliliters Soltrol ® 170 (a mixture of $C_{13}$–$C_{15}$ aliphatic hydrocarbons available from Phillips Chemical Co.). The reactions were repeated at different temperatures, the contents of the flask being heated to the temperature with stirring. Samples were removed at intervals for High Precision Liquid Chromatography (HPLC) analysis. The percent yield in these reactions 200° C., 160° C., and 125° C. are plotted as lines A, B, and C, respectively, against time in the graph illustrated in FIG. 3. The reaction at 200° C. was also repeated with potassium carbonate instead of potassium hydroxide. The results of this latter reaction is plotted as line D in FIG. 3. The superior yields over short reaction times with ordinary copper catalysts using the process of the instant invention is clearly apparent when comparing the yields and reaction times shown by curves A, B, and C compared to the yields and reaction times of curve D.

EXAMPLE XVI

Figure 4:
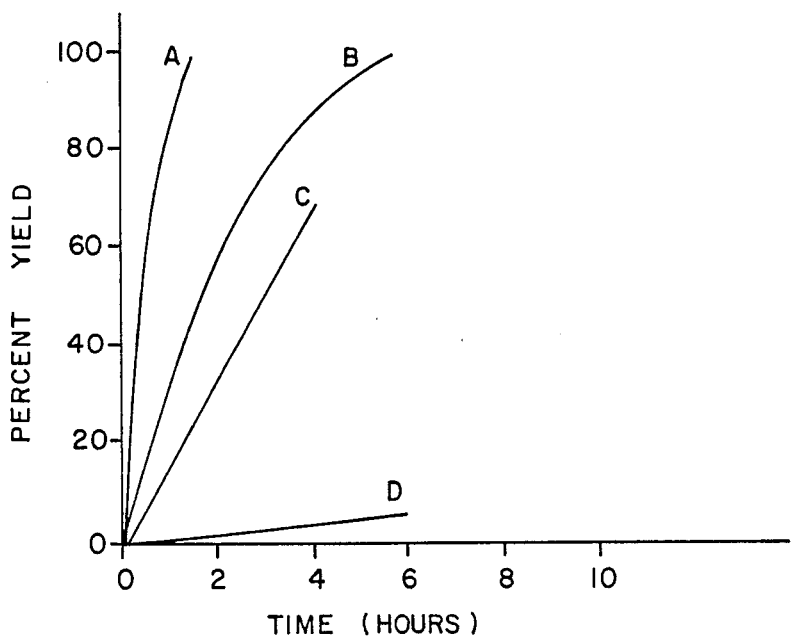
FIG. 4 graphically illustrates how different bases affect product yields.

Preparation of N,N'-diphenyl-N,N'-bis-(3-methylphenyl)-[1,1'-biphenyl]-4,4'-diamine in the presence of KOH, $K_2CO_3$, NaOH or $Li_2CO_3$ Into a 250 milliliter three-necked round bottom flask equipped with a mechanical stirrer, thermometer with a temperature controller and purged with argon was placed 10.3 grams of diiodobiphenyl (0.025 mole), 16.7 grams of 3-methyldiphenylbenzidine (0.1 mole) 7.5 grams Fisons #08 copper bronze and 15 milliliters Soltrol ® 170. Reaction runs were conducted with various different bases and plotted in the graph illustrated in FIG. 4. The amount of base added was 0.15 mole of each of the following different bases:

| | |
|---|---|
| KOH | 8.4 g |
| $K_2CO_3$ | 20.7 g |
| NaOH | 6.0 g |
| $Li_2CO_3$ | 11.1 g |

The reaction mixture was heated with stirring to 200° C. Samples were taken at intervals for HPLC analysis. The percent yield in these reactions involving KOH, $K_2CO_3$, NaOH, and $Li_2CO_3$ are plotted as lines A, B, C, and D, respectively, against time in the graph illustrated in FIG. 4. The superior yields of KOH over short reaction times with the best copper catalyst for the Creason et al process is clearly apparent when comparing the yields and reaction times shown by curve A against the yields and reactions times of curves B, C, and D.

EXAMPLE XVII

Preparation of N,N'-diphenyl-N,N'-bis-(3-methylphenyl)-[1,1'-biphenyl]-4,4'-diamine in the presence of KOH or $K_2CO_3$

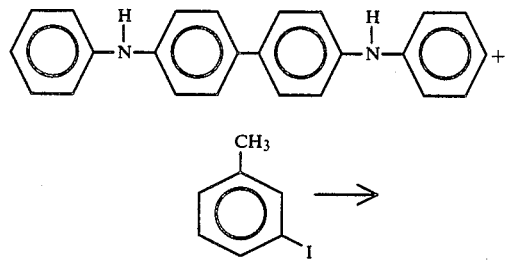

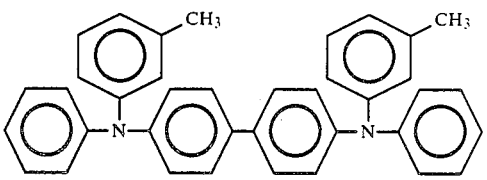

Into a 250 mls. three-necked round bottom flask equipped with a mechanical stirrer, thermometer with a temperature controller and purged with argon was placed 8.4 grams of N,N'diphenylbenzidine (0.025 mole), 16.3 grams of m-iodotoluene (0.075 mole), 11.2 grams of KOH flake (0.2 mole), 5 grams copper (Matheson, Coleman & Bell) and 15 milliliters of Soltrol ® 170. The contents of the flask were heated with stirring to 190° C. Samples were removed at intervals for HPLC analysis.

Into another 250 milliliter, three-necked round bottom flask equipped with a mechanical stirrer, thermometer with a temperature controller and purged with argon was placed 8.4 grams of N,N'diphenylbenzidine (0.025 mole), 20.7 grams of potassium carbonate (0.15 moles), 16.3 grams of m-iodotoluene (0.075 mole), 5 grams copper (Matheson, Coleman & Bell) and 15 milliliters Soltrol ® 170. The contents of the flask were heated with stirring to 190° C. Samples were removed at intervals for HPLC analysis.

Figure 5:
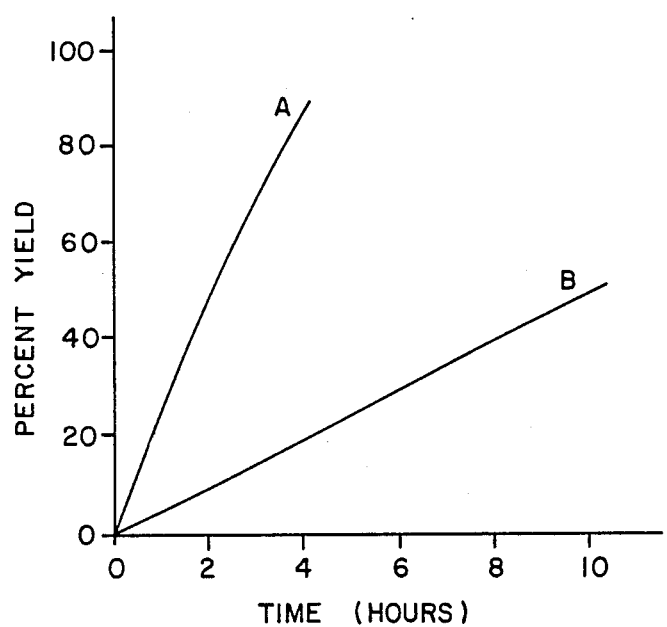
FIG. 5 graphically compares reactions employing KOH and K₂CO₃.

The percent yield in these reactions at 190° C. involving KOH and $K_2CO_3$ are plotted as lines A and B, respectively, against time in the graph illustrated in FIG. 5. The superior yields of KOH at 190° C. for short reaction times is clearly apparent when comparing the yields and reaction times shown by curve A against the yields and reaction times of curve B.

The invention has been described in detail with particular reference to preferred embodiments thereof but it will be understood that variations and modifications can be effected within the spirit and scope of the invention as described hereinabove and as defined in the appended claims.

What is claimed is:

1. In the reaction process of preparing a tertiary amine by the condensation of an amine selected from the group consisting of a mono- and a di-secondary amine and an aryl compound selected from the group consisting of a mono-iodoaryl compound and a di-iodoaryl compound, the improvement comprising conducting the condensation in the presence of potassium hydroxide, a copper catalyst, and with an inert saturated hydrocarbon solvent mixture of $C_{13}$–$C_{15}$ aliphatic hydrocarbons having an initial boiling point of at least about 170° C., in an inert atmosphere, at a temperature between about 120° C. to about 190° C. for a period of time sufficient to at least substantially complete the reaction.

2. In the reaction process of preparing a tertiary amine by the condensation of a mono-secondary amine having the general formula $R_2R_3NH$ wherein $R_2$ and $R_3$ are the same or different members selected from the groups consisting of alkyl, alkenyl, aryl, alkaryl and aralkyl, and a di-iodoaryl compound the improvement comprising conducting the condensation in the presence of potassium hydroxide, a copper catalyst, and an inert saturated hydrocarbon solvent having an initial boiling point of at least 170° C. in an inert atmosphere, at a temperature between about 135° C. to about 165° C. for a period of time sufficient to at least substantially complete the reaction.

* * * * *